United States Patent [19]

Voellmy et al.

[11] Patent Number: 5,346,812

[45] Date of Patent: Sep. 13, 1994

[54] TERATOGEN ASSAY

[75] Inventors: Richard W. Voellmy; Jayakumar Ananthan-Nair, both of Miami, Fla.

[73] Assignee: The University of Miami, Coral Gables, Fla.

[21] Appl. No.: 946,618

[22] Filed: Sep. 18, 1992

Related U.S. Application Data

[63] Continuation of Ser. No. 404,232, Sep. 7, 1989, abandoned.

[51] Int. Cl.[5] .................. C12Q 1/68; G01N 33/53; C12P 21/00
[52] U.S. Cl. .................................. 435/6; 435/7.1; 435/69.1; 435/69.7; 435/69.8; 435/18
[58] Field of Search .............. 435/69.1, 18, 7.1, 7.92, 435/6; 935/70, 59, 60; 800/2

[56] References Cited

U.S. PATENT DOCUMENTS 4,745,055  5/1988  Schenk et al. ................... 435/7.1

OTHER PUBLICATIONS

Bournias-Vardiabasis et al., Banbury Rep. 26: Developmental Toxicology: Mechanisms & Risk, Cold Spring Harbor Lab. (1987) pp. 3–16.
Lawson et al., Mol. Gen. Genetics 198:116–124 (1984).
Seecof, R. L. Preparation of cell cultures from Drosophila melanogaster embryos, Tissue Culture Association Manual 5(1):1019–1022, 1979.
Bournias-Vardiabasis, N., and R. L. Teplitz, Use of Drosophila embryo cell cultures as an in vitro teratogen assay, Teratog. Carcinog. Mutagen, 2:333–341, 1982.
Bournias-Vardiabasis, N., et al., Detection of teratogens in the Drosophila embryonic cell culture test: assay of 100 chemicals, Teratology 28:109–122, 1983.
Ritossa, F., A new puffing pattern induced by temperature shock and DNP in Drosophila, Experientia 18(12):571–573, 1962.

Craig, E. A., The heat shock response, CRC Crit. Rev. Biochem 18(3):239–280, 1985.
Sirotkin, K., and N. Davidson, Developmentally regulated transcription from Drosophila melanogaster chromosomal site 67B, Dev. Biol 89:196–210, 1982.
Mason, P. J., et al., The expression of heat shock genes during normal development in Drosophila melanogaster, Mol. Gen. Genet. 194:73–78, 1984.
Ireland, R. C., et al., Ecdysterone induces the transcription of four heat-shock genes in Drosophila S3 cells and imaginal discs, Dev. Biol. 93:498–507, 1982.
Buzin, C. H. and N. Bournias-Vardiabasis, The induction of a subset of heat-shock proteins by drugs that inhibit differentiation in Drosophila embryonic cell cultures, in Heat shock: from bacteria to man, M. J. Schlesinger et al., eds., Cold Spring Harbor Laboratory, Cold Spring Harbor, NY, pp. 387–394, 1982.

(List continued on next page.)

Primary Examiner—Margaret Parr
Assistant Examiner—Stephanie W. Zitomer
Attorney, Agent, or Firm—Sughrue, Mion, Zinn, Macpeak & Seas

[57] ABSTRACT

A method of screening a test substance for potential teratogenicity without employing vertebrate animals. In a representative embodiment, Drosophila primary embryonic cells, containing a hybrid game including a coding sequence for a detectable expression product under the control of a promoter sequence selected from among the 23 and 22 kDa Drosophila heat shock protein promoter sequences, are exposed to the test substance. The cells are thereafter assayed for the detectable expression product, the presence of the expression product in the cells providing an indication of the potential teratogenicity of the test substance. The primary embryonic cells containing the hybrid gene are conveniently provided by transformed flies.

3 Claims, 8 Drawing Sheets

OTHER PUBLICATIONS

Buzin, C. H., and N. Bournias-Vardiabasis, Teratogens induce a subset of small heat shock proteins in *Drosophila* primary embryonic cell cultures, *Proc. Natl. Acad. Sci. USA* 81:4075–4079, 1984.

Rubin, G. M., and A. C. Spradling, Genetic transformation of *Drosophila* with transposable element vectors, *Science* 218:348–353, 1982.

Di Nocera, P. P., and I. B. Dawid, Transient expression of genes introduced into cultured cells of *Drosophila*, *Proc. Natl. Acad. Sci. USA* 80:7095–7098, 1983.

Voellmy, R., et al., A DNA segment isolated from chromosomal site 67B in D. melanogaster contains four closely linked heat-shock genes, *Cell* 23:261–270, 1981.

Lawson, R., et al., Ecdysterone selectively stimulates the expression of a 23000-Da heat-shock protein—$\beta$-galactosidase hybrid gene in cultured *Drosophila* cells, *Dev. Biol.* 110:321—330, 1985.

Mestril, R., et al., Identification of a sequence element in the promoter of the *Drosophila melanogaster* hsp23 gene that is required for its heat activation, *EMBO J.* 4(11):2971–2976, 1985.

Mestril, R., et al., Heat shock and ecdysterone activation of the *Drosophila melanogaster* hsp23 gene: a sequence element implied in developmental regulation, *EMBO J.* 5(7):1667–1674, 1986.

Lis, J. T., et al., New heat shock puffs and $\beta$-galactosidase activity resulting from transformation of Drosophila with an *hsp*70-*lacZ* hybrid gene, *Cell* 35:403–410, 1983.

Voellmy, R., The heat shock genes: a family of highly conserved genes with a superbly complex expression pattern, *BioEssays* 1(5):213–217, 1985.

Southgate, R., et al., Nucleotide sequence analysis of the *Drosophila* small heat shock gene cluster at locus 67B, *J. Mol. Biol.* 165:35–37, 1983.

Lis, J. T., et al., A novel arrangement of tandemly repeated genes at a major heat shock site in *D. melanogaster, Cell* 14:901–919, 1978.

Bournias-Vardiabasis, N., and J. Flores, Drug metabolizing enzymes in *Drosophila melanogaster*: teratogenicity of cyclophosphamide in vitro, *Teratog. Carcinog. Mutag.* 3:255–262, 1983.

```
                                                                                    TACATCTATACATACACATAATATTTGCCGGTGCTGAT
                                                                                                                          -400
                                                                                                                                             -300
GCGACTTATCACTCCACCAGGCCTTTCATTCCACTCCCCTAGGAGATTGCTCATTTCCATAGCGATACTCTCACTTTCAATGCAGATAATGCGTA
                                -350                                  -250                                                                  -200
ATTGCGCAAATTCGAGAACTCTGCGATATTTCAGCCCGAGAAGTTTCGTGTCCCTTCTCGATGTCGATGTTTGTGCCCCTAGCACAGACACGAC
                                                    -150                                                                                    -100
GCGCACACACAGCGCCGACGGGCCCCGCGCACACTTCGACACGCAAGCGGTTGTATAAATATCCGGCACTTTCGTCAACCGGCGCTGCAGTTGAATTCAA
                                                            -50
AAGCCAAAGCGATAACAGCTAAAGCGAAAGTTATTCTTTGAAGGAGGAGAATCATCTTGAAGCAATTAAAAACAAAA
              15                              30                              45                                    60                    75
ATG GCA AAT ATT CCA TTG TTG AGC GAT TTG GCC GAT TTG AGC CTT GCC GAT TTG GGC CGA ATG TCG ATG GTG CCC TTC TAT GAG CCC
MET ALA ASN TLE PRO LEU LEU SER   ASN ARG  ARG ASN PRO  LEU ALA LEU ALA ASP LEU SER  GLY ARG MET SER MET VAL PRO PHE TYR GLU PRO
                                90                              120                                  135                                   150
TAC TAC TGC CGC CAG AGG AAT CCC TAC TTG GCC CTG GTT GGA CCG ATG CAG GAG CTG CGC CAG CTG GAG
TYR TYR CYS ARG GLN ARG ASN PRO TYR LEU ALA LEU VAL GLY PRO MET GLN GLU LEU ARG GLN LEU GLU
                  165                                     195                                       210                                 225
AAA CAG GTG GGC GCC TCG GGA TCG GTG TCG GGA AAA ATC GGA AAG GAT GGC TTC CAG GTC TGC ATG
LYS GLN VAL GLY ALA SER GLY SER VAL SER   GLY LYS ILE GLY TLE LYS ASP GLY PHE GLN VAL CYS MET
                  240                                     270                                       285                                 300
GAT GTG TCG CAC TTC AAG CCC AGC GAA GTG GTC AAA CTG GAC AAC TCC CTG GTG GAG GGC AAC CAT
ASP VAL SER HIS PHE LYS PRO SER GLU VAL VAL LYS LEU ASP ASN SER LEU VAL GLU GLY ASN HIS
              315                                 345                                   360                                          375
GAG GAG CGC GAT GAC CAT TTC ATC CGT CAC TTT GTC CGC TAT GCT CTG CCA CCC GGT TAT GAG
GLU GLU ARG ASP ASP HIS  ILE PHE ARG HIS PHE VAL ARG ARG TYR ALA LEU PRO PRO GLY TYR GLU
              390                                     420                                   435                                       450
GCT GAT AAG GTG GCC TCC ACC TTG TCC GAT GGT GTC CTG ACC ATC AAG GTG CCC CCA CCG GCA ATC GAG
ALA ASP LYS VAL ALA SER THR LEU SER ASP GLY VAL LEU THR ILE LYS VAL PRO PRO PRO ALA ILE GLU
              465                                     495                                      510                                    525
GAT AAG GGC AAC GAG CGC ATC GTT CAG ATC CAG CAG GGA CCC GCC CAT GTG AAG GAG AAT CCC AAG
ASP LYS GLY ASN GLU ARG ILE VAL GLN ILE GLN GLN GLY PRO ALA HIS VAL LYS GLU ASN PRO LYS
              540                                          570                                                          600
GAG GCG GTG GAG CAG CAG GAC AAT GGC GAT AAG TAG AGGACTCGTTCCGGAGATGCCCTGCTTTAATCTTAGTTTGGAATATGTATTA
GLU ALA VAL GLU GLN GLN ASP ASN GLY ASP LYS   AM
                                                                     750                                    800
ACATCTGTTTTTATAAGCTGTAGTTATCCAAGGACACTTCACTCATACACAATAGCCATTAAGGGTGTCCTGCTTTAATCTTAGTTTGGAATATGTATTA
                                                   850                                                      900
CTAAATTGGCGAAATTAATATTACCCATAAAAATAACAAGTACACTTACTTATATAATTGTGTTCTGTTTTTCTGGTTATGGGTTACTA
                                    950
TTACTATTACTATTCTCGGAATTGTTTGGGTAGCTCGGCCCTTTTCCTGTGATCCCGGTTCTAGATTTACTTCTGCATTGTATATTGCATTGTT

GTGTCACGTAAAATGGCATTTTTATTTAATTGTGTTTGTGTACATAACTGACTTTTTACATTACTTCGGTAAAGAGTCTTGAAGC
```

Figure 3

|  |  | • -550 |  |  |
|---|---|---|---|---|
|  | CCAT | GGGTCATTAC -500 | CTACCCGGCA | TTAACCACTT |
| ATGTATGTAT | TTTAATTAGA | TTTCCCCACT -450 | ACAGAGCCCC | ATTCTTGGAT |
| ATTAATTAAA | GTTAATAGCT | TAAATGCAAG -400 | GCCATAAAAA | GAAGAACTGT |
| TCTGCTGTCT | CGAAGTTTCG | CGAATTTACT -350 | CCATCCTTCG | TGGAATATAC |
| TTCAACCTTC | CTATCTGCTA | TGTATGTACA -300 | TACATACGTG | CTTACATACG |
| TACATCTATA | CATACACATA | ATATTTGCCG -250 | GTGCTGATGC | GACTTATCAC |
| TCCACCAAGC | CTTTTCATTC | CCACTCCCCT -200 | AGGAGATTGC | TCATTTTCCA |
| TAGCGATACT | CTCACTTTCA | ATGGCAGATA -150 | ATGCGTAATT | GCGGCAAATT |
| CGAGAACTCT | GCGATATTTT | CAGCC CGAGA -100 | AGTTTCGTG T | CCCTTCTCGA |
| TGTCGATGTT | TGTGCCCCCT | AGCACACAGA -50 | CACGACGCGC | ACACACACAG |
| CGCCGACGGG | CGCACGCACA | CTTCGACAGC +1 | AAGCGGTTG T | ATAAATA TCC |
| GGCACTTTCG | TGCAACCGGC | GTCAGTTGAA | TTCAAAAAGC | CAAAAGCGAT |

TERATOGEN ASSAY

This application is a continuation of Ser. No. 07/404,232 filed Sep. 7, 1989 and now abandoned.

FIELD OF THE INVENTION

This invention relates to the field of toxicology, and particularly to teratology.

BACKGROUND OF THE INVENTION

Teratogenesis, the formation of congenital defects, was recognized early in this century as an illness and as an important cause of morbidity and mortality among newborns. In 1928 Murphy published a study in which he followed 320 human pregnancies and found 14 cases of children with small head circumference and mental retardation. The defect was ascribed to therapeutic irradiation of the mothers of these children early in their pregnancies. Viruses and nutritional deficiencies were also shown to be potentially teratogenic.

The drug thalidomide, a sedative-hypnotic, was introduced in the late 1950s. Use of this drug by pregnant women resulted in some 10,000 babies suffering from phocomelia, a normally rare congenital malformation with shortening or absence of limbs. The impact of the teratogenic effect of this drug led society to attempt to actively prevent the introduction for human consumption of teratogenic drugs. It became mandatory to subject new drugs, foods, pesticides, or contaminants to different types of tests to determine their potential teratogenicity.

The standard practice for testing a new drug for teratogenicity typically involves studies with more than one kind of animal. Mammalian species such as rats, rabbits, mice, and hamsters are commonly used. Pigs are sometimes used because of their relatively close phylogenetic relationship with humans, and because their diet is similar to that of humans. Dogs, cats, and nonhuman primates have also been employed. These available assays are time-consuming and expensive. In recent years, societal pressure has increased dramatically to limit and, wherever possible, find substitutes for tests involving vertebrate and particularly mammalian animals.

Teratogen assays involving fruit-fly cells has been previously described. The preparation of primary embryonic cell cultures from 3 to 8 hour old Drosophila (fruit-fly) embryos has been described in some detail (Seecof, R. L., Tissue Culture Association Manual 5, 1019–1022, 1979). Cells in these cultures differentiate in vitro to myotubes and ganglia. A teratogen assay based on inhibition of these differentiation processes has been reported (Bournias-Vardiabasis, N., and R. L. Teplitz, Teratog. Carcinog. Mutagen. 2:333–341, 1982; Bournias-Vardiabasis, N., et al., Teratology 28:109–122, 1983). This inhibition would have to be assessed by microscopic observation, and so this assay would be semi-quantitative as well as tedious to perform.

Heat shock genes are a group of genes that occur in apparently all living organisms and that are typically silent at the normal temperature of growth of the organism but are activated at somewhat elevated temperatures. (For a review, see: Schlesinger, M. F., et al., ed., Heat shock: From bacteria to man, Cold Spring Harbor Laboratory, Cold Spring Harbor, N.Y., 1982). The genes have been discovered in the fruit fly Drosophila (Ritossa, F., Experientia 18:571–575, 1962). The fly genes are silent at moderate temperatures but become very active at temperatures between 35° and 38°-39° C.

Heat shock genes were cloned initially from Drosophila and more recently also from many other organisms (see Craig, E. A., CRC Crit. Rev. Biochem. 18:239–280, 1985, for a review). Drosophila melanogaster has one gene encoding an 83 kDa heat shock protein (hsp83), 5 genes encoding the major 70 kDa heat shock protein (hsp70), and one gene encoding each of four small heat shock proteins with molecular weights of 27, 26, 23, and 22 kDa (hsp27, hsp26, hsp23, and hsp22). The small heat shock protein genes are also highly active (at normal temperatures) during certain distinct stages of normal development; they are all expressed at relatively high levels in late third instar larvae, during which the titer of the molting hormone ecdysterone is maximal (Sirotkin, K., and N. Davidson, Dev. Biol. 89:196–210, 1982; Mason, P., et al., Mol. Gen. Genet. 194:73–78, 1984). This finding suggested that the small heat shock genes may be regulated directly or indirectly by ecdysterone. Strong evidence for this was provided by experiments that demonstrated activation of the genes in cultured Drosophila cells or isolated imaginal discs following the addition of ecdysterone to the medium (ireland, R., et al., Dev. Biol. 93:498–507, 1982).

Buzin and Bournias-Vardiabasis recognized that the same set of drugs that inhibited differentiation of embryonic Drosophila cells in vitro, also caused activation of two of the small heat shock protein genes, encoding the 23 and 22 kDa protein species. In these experiments heat shock protein synthesis was monitored by $^{35}$S-methionine-labeling of proteins and autoradiography of two-dimensional electrophoresis gels (Burzine, C. H., and N. Bournias-Vardiabasis, in Heat shock: from bacteria to man, M. J. Schlesinger, et al., eds., Cold Spring Harbor Laboratory, Cold Spring Harbor, N.Y., pp. 389-394, 1982; Proc. Natl. Acad. Sci. USA 81:4075–4079, 1984).

By the mid-1980s, at least three methods were available for transfection and measuring transient expression of genes in Drosophila cells (Rubin, G. M., and A. C. Spradling, Science 218:348–353, 1982; DiNocera, P. P., and I. P. Dawid, Proc. Natl. Acad. Sci. USA 80:7095–7098, 1983; Lawson, R., et al., Mol. Gen. Genet. 198:116–124, 1984).

The Drosophila melanogaster 23 kDa heat shock protein gene has been cloned and characterized by Voellmy et al. (Cell 23:261-270, 1981). Segments containing extensive 5' nontranscribed sequences from the 23 kDa heat shock protein gene, the RNA leader region, and part of the protein-coding region were linked in frame to an E. coli β-galactosidase gene. The resulting constructs encode a hybrid protein with β-galactosidase activity that is made under the control of the linked heat shock gene sequences (Lawson, R., et al., Dev. Biol. 100:321-330, 1985). These constructs were introduced into Drosophila melanogaster S3 cells (an established cell line) by transfection (Lawson, R., et al., Mol. Gen. Genet. 198:116-124, 1984). The transfected hybrid genes produced E. coli-specific β-galactosidase in response to heat treatment or ecdysterone addition to the medium (Lawson, R., et al., Dev. Biol. 110:321-330, 1985; Mestril, R., et al., EMBO J. 4(11):2971-2976, 1985; Mestril, R., et al., EMBO J. 5(7):1667-1673, 1986).

The established procedure of P-element-mediated transduction of genes in Drosophila melanogaster has been described in detail (Rubin, G. M., and A. C. Spradling, Science 218:348-353, 1982) has is frequently used to introduce genes of interest into the germline. A hybrid gene that consists of the Drosophila heat shock gene, hsp70, fused to the E. coli β-galactosidase gene has been introduced into the Drosophila germline by the P-element microinjection method. The β-galactosidase activity in the transformants was reportedly inducible by heat shock and showed a widespread distribution throughout the tissues of larvae and adults (Lis, J. T., et al., Cell 35:403–410, 1983).

SUMMARY OF THE INVENTION

The invention provides a method of screening a test substance for potential teratogenicity, conveniently and rapidly, without employing vertebrate animals. In a representative embodiment, Drosophila primary embryonic cells, containing a hybrid gene including a coding sequence for a detectable expression product under the control of a promoter sequence selected from among the 23 and 22 kDa Drosophila heat shock protein promoter sequences, are exposed to the test substance. The cells are thereafter assayed for the detectable expression product, the presence of the expression product in the cells providing an indication of the potential teratogenicity of the test substance. The primary embryonic cells containing the hybrid gene are conveniently provided by transformed flies.

BRIEF DESCRIPTION OF THE DRAWINGS

FIG. 2 (prior art) shows the nucleotide sequence of the coding region and flanking sequences of the Drosophila 23 kDa heat shock protein gene (hsp23);

DETAILED DESCRIPTION OF THE PREFERRED EMBODIMENT

The invention provides convenient and rapid assays of the teratogenic potential of drugs and other substances, without employing vertebrate animals. The subject assays are based upon the discovery that the expression of small 23 and 22 kDa heat shock protein genes is induced in primary embryonic Drosophila cells upon exposure of the cells to teratogens. Furthermore, since heat shock protein gene expression cannot be quantified easily and accurately by the average clinical laboratory by methods that involve labeling of proteins with radioactive amino acids and one- or even two-dimensional gel electrophoresis, or measurements of transcript levels by necleic acid hybridization, two procedures are provided that achieve the above goal.

First, transformed flies have been developed that carry a conveniently detectable marker gene that has been placed under the control of a promoter from one of the small inducible heat shock protein genes. Teratogenic potentials can now be measured by a colorimetric assay of marker gene expression in embryonic cells, derived from these transformed flies, that have been exposed to substances of interest. The second procedure involves antibodies specific for the product of the marker gene, and their use in immunological procedures such as ELISA to measure antigen concentrations in the cells following exposure to drugs of interest.

In a representative embodiment, Drosophila primary germ cells, containing a hybrid gene including a coding sequence for a detectable expression product under the control of a promoter sequence selected from among the 23 and 22 kDa Drosophila heat shock protein promoter sequences, are exposed to the test substance. The cells are thereafter assayed for the presence of the detectable expression product, which indicates the potential teratogenicity of the test substance.

The term "primary embryonic cells" as used herein is meant to include Drosophila gastrulation stage embryologic ells, cell cultures prepared from such cells, and postgastrulation embryonic cells, either within larvae or cell culture, that are characterized by differentiation of myoblasts and neuroblasts which is susceptible to inhibition by teratogens. The primary embryonic cells are engineered to contain (or, preferably, are derived from engineered germ cells that contain) a hybrid gene that directs the expression of a detectable product when the cells are exposed to potential teratogens.

The hybrid gene contains a DNA coding sequence for a detectable expression product such as β-galactosidase. Appropriate expression products are characterized by being detectable in the cells or homogenates of the cells using available colorimetric, immunologic, or other assay procedures. Representative coding sequences that are readily available and suitable for this purpose include DNA encoding for β-galactosidase, bacterial chloramphenicol acetyltransferase, luciferase, etc.

The hybrid gene also contains a promoter sequence that controls the transcription of the coding sequence in the primary embryonic cells. Appropriate promoter sequences are selected from the DNA sequences 5' flanking the start codons of Drosophila genes that are induced or preferentially expressed by teratogens. Representative promoter sequences for this purpose include teratogen-inducible 5' regions from the Drosophila 23 and 22 kDa heat shock protein genes.

The hybrid gene preferably also contains a leader sequence positioned between the promoter sequence and the coding sequence. The leader sequence is selected to enhance the translation of the coding-sequence mRNA in the primary embryonic cells. Representative leader sequences for this purpose include the leader sequences from the 23 and 22 kDa heat shock protein genes.

The hybrid gene may also contain a nontranscribed and nontranslated sequence positioned 3' to the coding sequence. Appropriate 3' nontranscribed sequences are selected to contain a transcription terminator signal and/or to facilitate or enhance post-transcriptional processing of the detectable expression product in the primary embryonic cells.

A representative hybrid gene in accordance with the above description includes a 23 kDa heat shock protein gene fragment beginning at the Pst I site 1.5 kb upstream from and extending through the transcription start site and the entire RNA leader region to a Pvu II site at codon 45 of the 23 kDa protein coding sequence, inserted upstream from a truncated (at codon 7 or 8) *E. coli* β-galactosidase gene. It addition, a 2.4-kb-long segment containing 3' nontranslated and nontranscribed sequences from a *D. melanogaster* 70 kDa heat shock protein gene is placed downstream from the β-galactosidase gene. The resulting construct directs the synthesis of β-galactosidase in *D. melanogaster* primary embryonic cells prepared from transformed files (but not in immortalized S3 cells) following exposure to teratogens such as thalidomide and lead.

The hybrid gene is introduced by established transfection protocols. In a preferred embodiment, Drosophila embryos are transformed with the hybrid gene using the established P-element transformation technique. Adult files are then raised from the transfected embryos and, after appropriate crosses, are used as a source of embryos to prepare the primary embryonic cells (containing the hybrid gene) for the subject assay.

The representative assays of teratogenic potential presented here are based on measurements of the expression of the 23 kDa Drosophila heat shock protein and/or of the activity of the promoter of the gene encoding this protein. The published literature reported that known mammalian teratogens induced both 23 and 22 kDa heat shock proteins in embryonic cells, and that lack of accumulation of these proteins followed exposure to known nonteratogens. (Buzin, C. H., and N. Bournias-Vardiabasis, *Proc. Natl. Acad. Sci. USA* 81:4075–4079, 1984.) However, the mechanism or mechanisms (mechanisms could be different for different teratogens) underlying the observed accumulation of specific heat shock proteins were not reported at all. Possible mechanisms include stabilization of the heat shock proteins that might be achieved in a number of different ways, stabilization of the messenger RNAs encoding these proteins, enhancement of the translatability of these messenger RNAs, enhancement of the transport of the messenger RNAs from nucleus to cytoplasm, or enhancement of transcription of the genes encoding the proteins. A priori, any of these mechanisms could account for the published observations. The approach demonstrated here, involving the use of hybrid genes consisting of promoter and RNA leader elements from the Drosophila 23 kDa heat shock protein gene and a convenient marker gene such as a bacterial β-galactosidase gene, could only work if the teratogen-induced heat shock protein accumulation was based on either transcriptional regulation or on a posttranscriptional type of regulation that is targeted exclusively to the RNA leader region of the small heat shock protein genes. That it does work represents a novel finding and indicates that regulation of protein accumulation is mediated by one of the latter mechanisms.

Furthermore, in the case of a control mechanism that operates at the transcriptional level, transformed fly strains or cell lines containing teratogen-responsive heat shock - marker hybrid genes could only be obtained if the transcriptional control elements were relatively close to the start-of-transcription site of the heat shock gene concerned. Upstream sequences that are more than about 1.5 kb away from the start site could only have been employed with difficulties, and the use of sequences more than about 15 kb away from the start site was essentially precluded for technical reasons. Fortunately, the 554 bp promoter used for the prototype teratogen assay is induced by teratogens and so provided for an operable and useful assay.

In addition, the stability of the marker gene product in Drosophila cells is also of importance: A labile marker gene product could never accumulate. Conversely, a very stable marker gene product would accumulate even in the absence of teratogens (due to low levels of noninduced activity of the promoter), resulting in intolerably high background levels in the teratogen assay.

The invention thereby provides assays for estimating, in an industry or regulatory setting, the teratogenic potential of substances to be used by humans or likely to get into contact with humans. The subject assays are based on measurements of the expression discrete genes in differentiating cultured cells derived from the fruit fly *Drosophila melanogaster*. These assays can be completed within 24 to 48 hrs and are useful (a) for the prescreening of new drugs, foods, pesticides, etc., concerning their potential teratogenicity without having to use mammalian animals, and (b) as an additional approach to complement the traditional animal experiments to detect potential human teratogens.

The invention is further illustrated by the following representative examples.

EXAMPLE 1

Structure of Drosophila small heat shock protein hybrid genes

Figure 1:
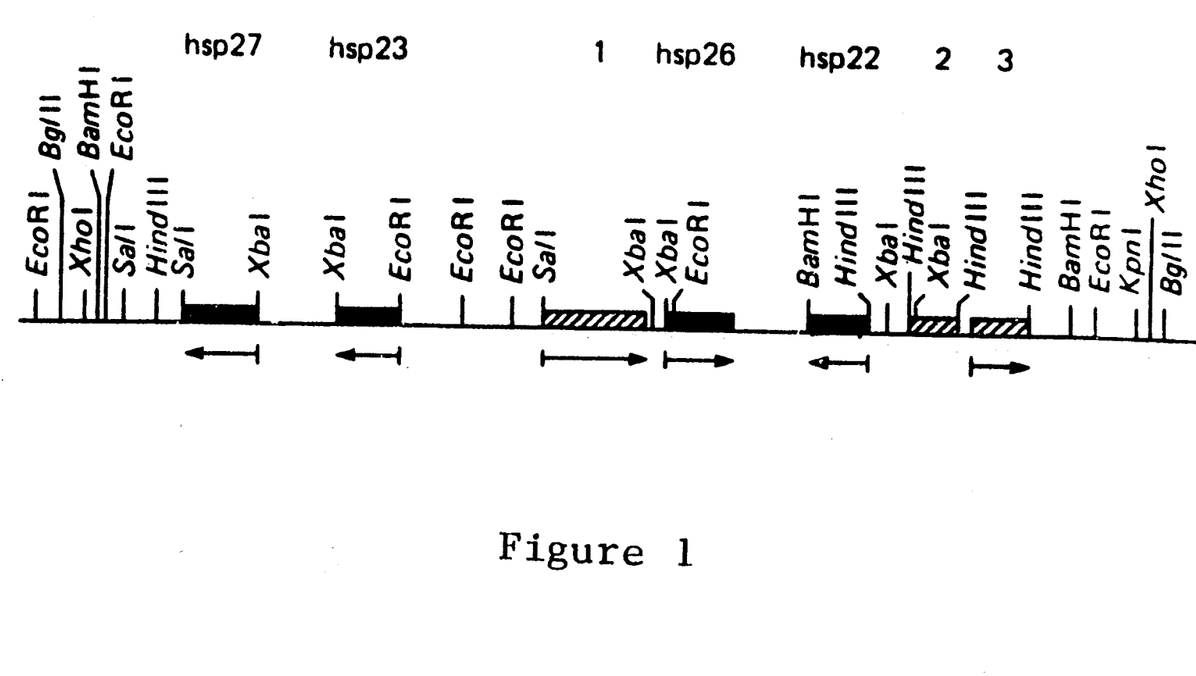
FIG. 1 (prior art) is a map of the 67B locus containing all four of the small heat shock protein genes from Drosophila, genes 1-3 are non-heat-shock genes.

The isolation of the Drosophila small heat shock protein genes has been described in detail by Voellmy et al. (*Cell* 23:261–270, 1981) and other research groups. The region from locus 67B contains a gene cluster that includes the four small heat shock protein genes (see FIG. 1); as previously published in Voellmy, R., *BioEssays* 1:213–217, 1985). A Pst I fragment that included the 23 kDa heat shock protein gene and about 1.5 kb of 5' nontranscribed sequence was subcloned into the Pst I site of vector pSVOd. The resulting subclone, F4.17, has been described previously (Lawson, R., *Dev. Biol.* 110:321–330, 1985). Plasmid F4.17 has been deposited under accession No. 40653 at the American Type Culture Collection, 12301 Parklawn Drive, Rockville, Md., U.S.A. 20852.

Figure 3:
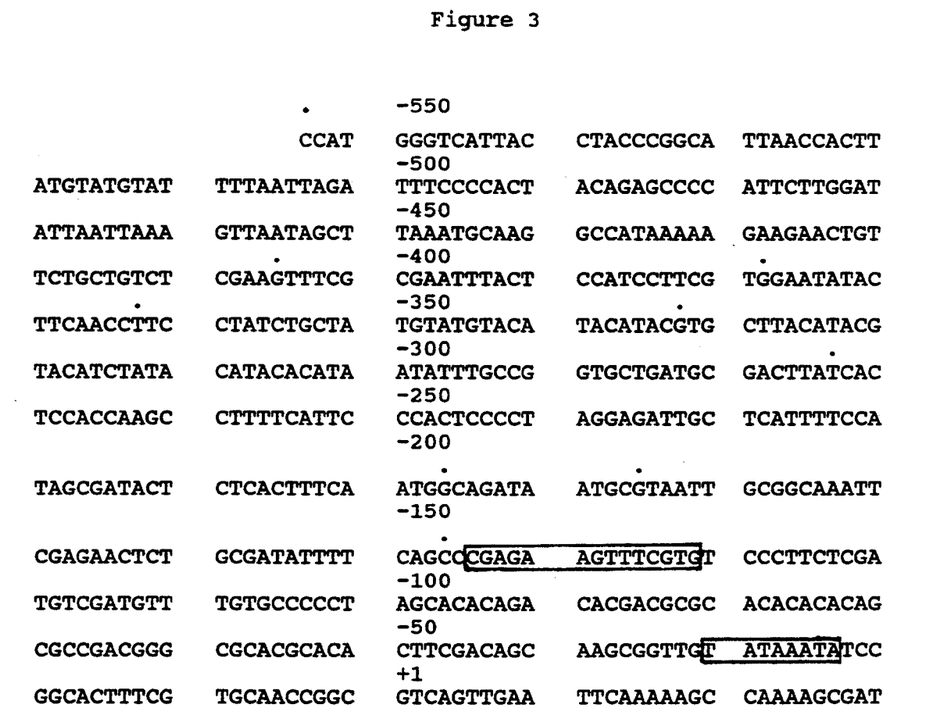
FIG. 3 (prior art) shows the nucleotide sequence of the hsp23 promoter, +1 refers to the start of transcription site; the TATA motif and the −132 HSR are boxed; and the dots indicate endpoints of promoter segements in 5' deletion mutants.

The nucleotide sequence of the 23 kDa heat shock protein gene is shown in FIG. 2 (as previously published in Southgate, R., et al., *J. Mol. Biol.* 185:35–57, 1983), and the sequence of the 5' nontranscribed region, as far as it is known, is shown in FIG. 3 (as previously published in Mestril, R., et al., *EMBO J.* 5:1667–1673, 1986).

Figure 4:
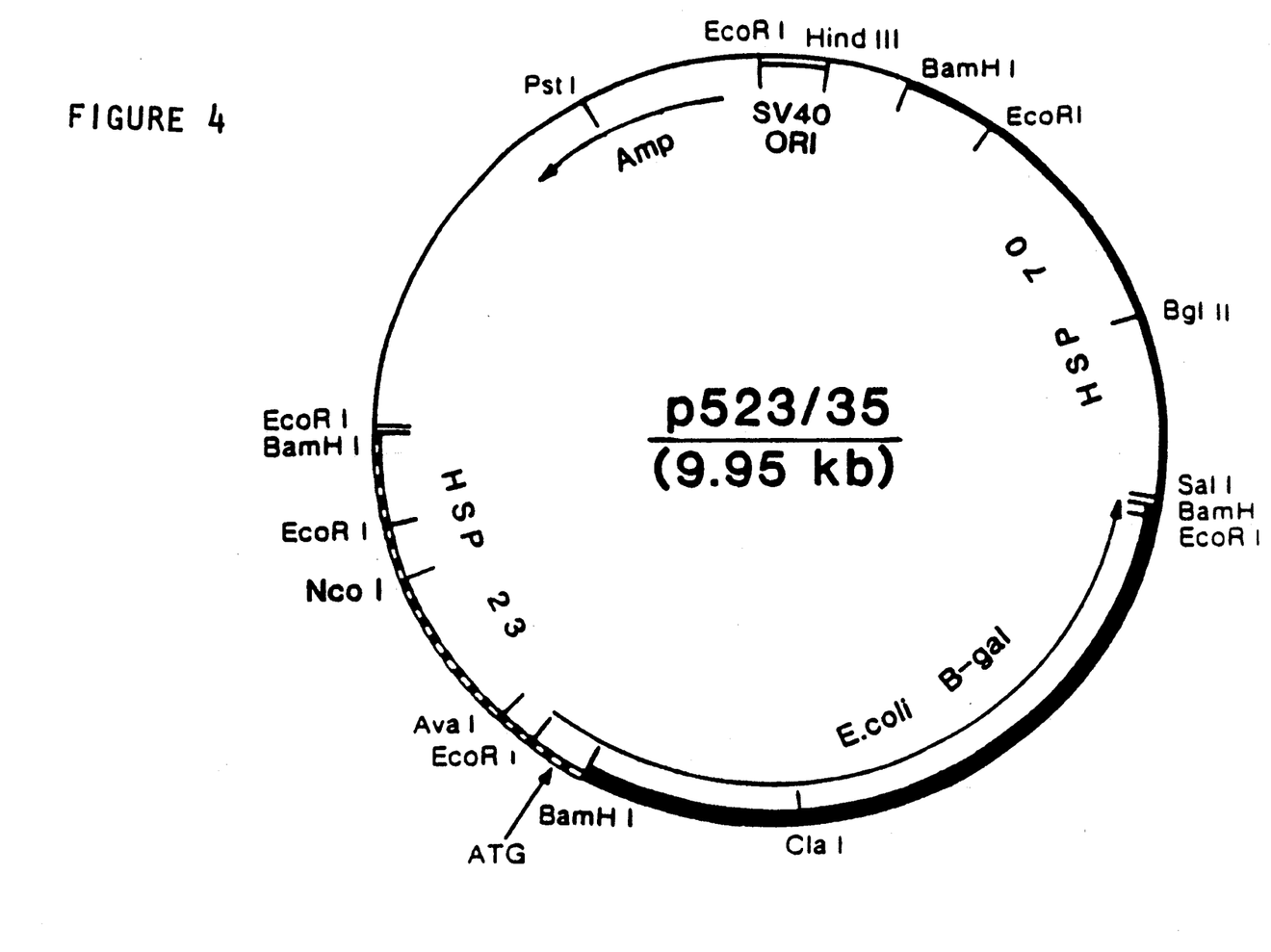
FIG. 4 (prior art) is a map of a 23 kDa heat shock protein-β-galactosidase hybrid gene in a representative plasmid p523/35.

The construction of 23 kDa heat shock protein-β-galactosidase hybrid genes had been described (Lawson, R., et al., *Dev. Biol.* 110:321–330, 1985). The structure of a representative construct, p523/35, is shown in FIG. 4 (modified from Mestril, R., et al., *EMBO J.* 5(7):1667–1673, 1986). Briefly, a *D. melanogaster* 23 kDa gene fragment beginning at the Pst I site 1.5 kb upstream from and extending through the transcription start site and the entire RNA leader region to a Pvu II site at codon 45 of the 23 kDa heat shock protein-coding sequence (obtained from subclone F4.17) was inserted upstream from a truncated (at codon 7 or 8) E. coli β-galactosidase gene. In addition, a 2.4 kb-long segment containing 3' nontranslated and nontranscribed sequences from a D. melanogaster 70 kDa heat shock protein gene was downstream from the β-galactosidase gene. The resulting construct directed the synthesis of β-galactosidase in transfected D. melanogaster S3 cells following heat treatment or exposure to ecdysterone. Hybrid gene activity was assessed in cell extracts both by a colorimetric enzymatic assay and by ELISA using antibodies specific for E. coli β-galactosidase (Lawson, R., et al., Dev. Biol. 110:321–330, 1985).

Derivatives of this basic construct that contained 23 kDa heat shock gene promoter sequences of different lengths were prepared, and their activity was tested using heat shock in transfected S3 cells (Mestril, R., et al., EMBO J. 4:2971–2976, Mestril, R., et al., EMBO J. 5:1667–1673, 1986). While heat shock worked, exposure to teratogens such as coumarin did not induce hybrid gene activity in the S3 cells.

EXAMPLE 2

Construction of P-element-vectors containing 23 KDa heat shock-β-galactosidase hybrid genes In order to introduce the hybrid genes into the D. melanogaster germline (see Rubin, G. M. and A. C. Spradling, Science 218:348–353, 1982, for a description of the technology) it was necessary to excise them from their normal vector (Mestril, R., et al., EMBO J. 5:1667–1673, 1986) and to insert them into a specialized vector containing transposable element sequences (P-element) as well as a marker gene that permitted selection of successfully transformed flies. Vector cp20.1 (available from Dr. J. T. Lis, Cornell University) that contained a rosy (eye color) gene was used.

Figure 5:
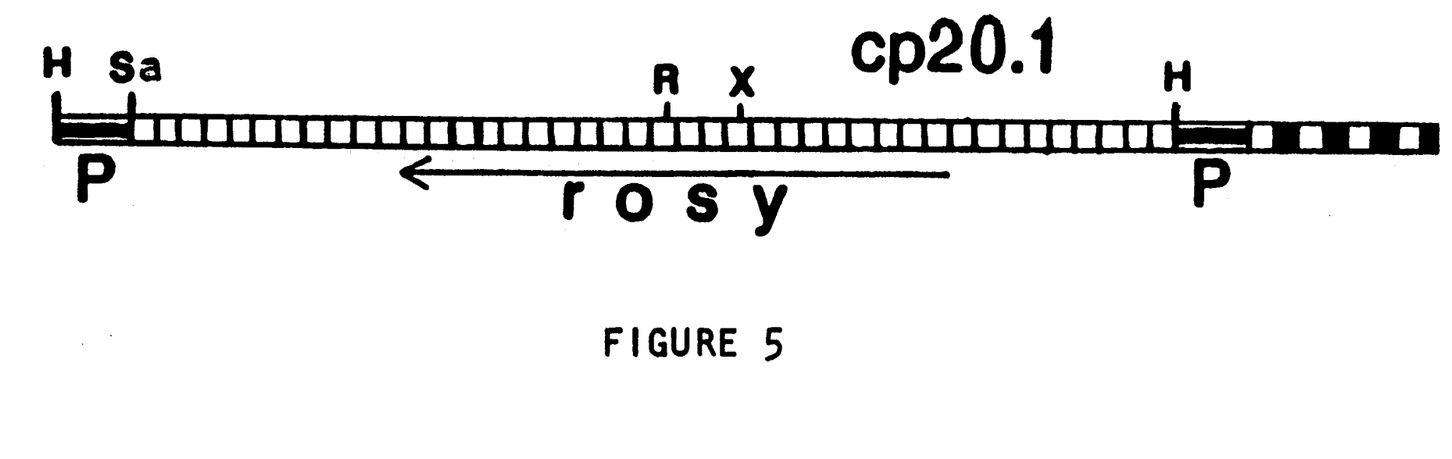
FIG. 5 (prior art) is a map of a representative P-element vector cp20.1; H is Hind III, Sa is Sal I, R is EcoRI, X is XhoI and P is P-element sequences.

The hybrid genes where to be introduced into the unique Sal I site of vector cp.20.1 (FIG. 5). To achieve this, an auxiliary construct, p671SX, had to be prepared. Plasmid 671SX is identical to pS671 (Lawson et al., Mol. Gen. Genet. 198:116–124, 1984) except that a Bgl Ii site about 1 kb downstream from the β-galactosidase-coding region (see FIG. 6) had been Xho I site, and that the Sal I site as the end of the coding region had been destroyed. In detail, 5 μg of p671 DNA were digested with 20 units of Sal I (New England Biolabs; buffers used according to manufacturer's recommendations) for 2 hrs at 37° C. The digested DNA was then precipitated by the addition of 1/20 volume of 5N NaCl and 3 volumes of ethanol, refrigeration to −20° C. and centrifugation in an Eppendorf desktop centrifuge. The pellet was washed once with 70% ethanol, dried, dissloved in a small volume of water and added to 50 μl of Klenow reaction mixture (Maniatis, T., et al., Molecular cloning: a laboratory manual, Cold Spring Harbor Laboratory Press, Cold Spring Harbor, N.Y., 1982) containing all four deoxynucleotide triphosphates, at concentrations of 0.25 mM, and 2 μl of DNA polymerase I Klenow fragment (New England Biolabs). After 20 min of incubation at room temperature, the DNA was extracted two times with phenol and three times with ether. Subsequent to ethanol precipitation of the DNA was washed, dried, and dissolved again in a small volume of water, and one third of this DNA was added to a 25 μl ligation mixture containing 2 μl of T4 DNA ligase (ligation buffer according to Maniatis et al., 1982, supra; T4 DNA ligase from New England Biolabs).

Following overnight incubation at 15° C., the ligase was inactivated by incubation for 10 min at 65° C. One μl of a solution of bovine serum albumin (5 mg/ml) in water and 8 units of Sal I were added, and the reaction was incubated for 2 hrs at 37° C. The reaction mixture was subsequently used to transform competent E. coli MC1061 cells. (A standard transformation protocol, such as that described in Maniatis et al., 1982, supra, was employed.) Bacteria from individual ampicillin-resistant colonies were grown in 1 ml cultures, and DNA was prepared in small quantities according to the lysozyme boiling procedure of David S. Holmes (published in BioTechniques). The DNAs were then digested with Sma I (which cuts once at the 5' end of the truncated β-galactosidase gene) and Sal I. The absence of the Sal I site was verified by electrophoresis of the RNase-treated digests on a 0.9% neutral agarose gel. Serveral recombinants that lacked a Sal I site were identified. DNA of one such plasmid (p671S) was prepared in larger quantities.

Five μg of p671S DNA were digested in a volume of 50 μl with 20 units of Bgl II (New England Biolabs; buffers recommended by supplier were used) for 2 hrs at 37° C. All four deoxynucleotide triphosphates (dATP, dCTP, dGTP, and dTTP) were then added to a final concentration of 0.23 mM. Two μl Klenow fragment of DNA polymearse I (New England Biolabs) were added, and the reaction was incubated for 20 min at room temperature. Following two phenol and three ether extractions the DNA was ethanol-precipitated and collected by centrifugation. The pellet was washed once with 70% ethanol, dried, resuspended in water, and the DNA was added to 100 μl of ligation buffer (New England Biolabs' specification) containing 2 μg of phosphorylated Xho I linkers (New England Biolabs) and T4 DNA ligase (3 μl; New England Biolabs). The ligation reaction was incubated overnight in the refrigerator. The ligase was then inactivated by incubation at 65° C. for 10 min. Following addition of 10 μg of bovine serum albumin and several units of Bgl II, the reaction mixture was incubated for 2 hrs at 37° C. and was subsequently used to transform E. Coli strain MC1061. Plasmid DNA' were prepared from different colonies. The DNA' were then subjected to Cla I/Xho I double digestion followed by RNase treatment and electrophoresis in a 0.9% neutral agarose gel. Digests that contained a 3 kb-long fragment were indicated for plasmids of the 671SX type. Larger quantities of DNA of one such plasmid were then prepared.

Figure 6:
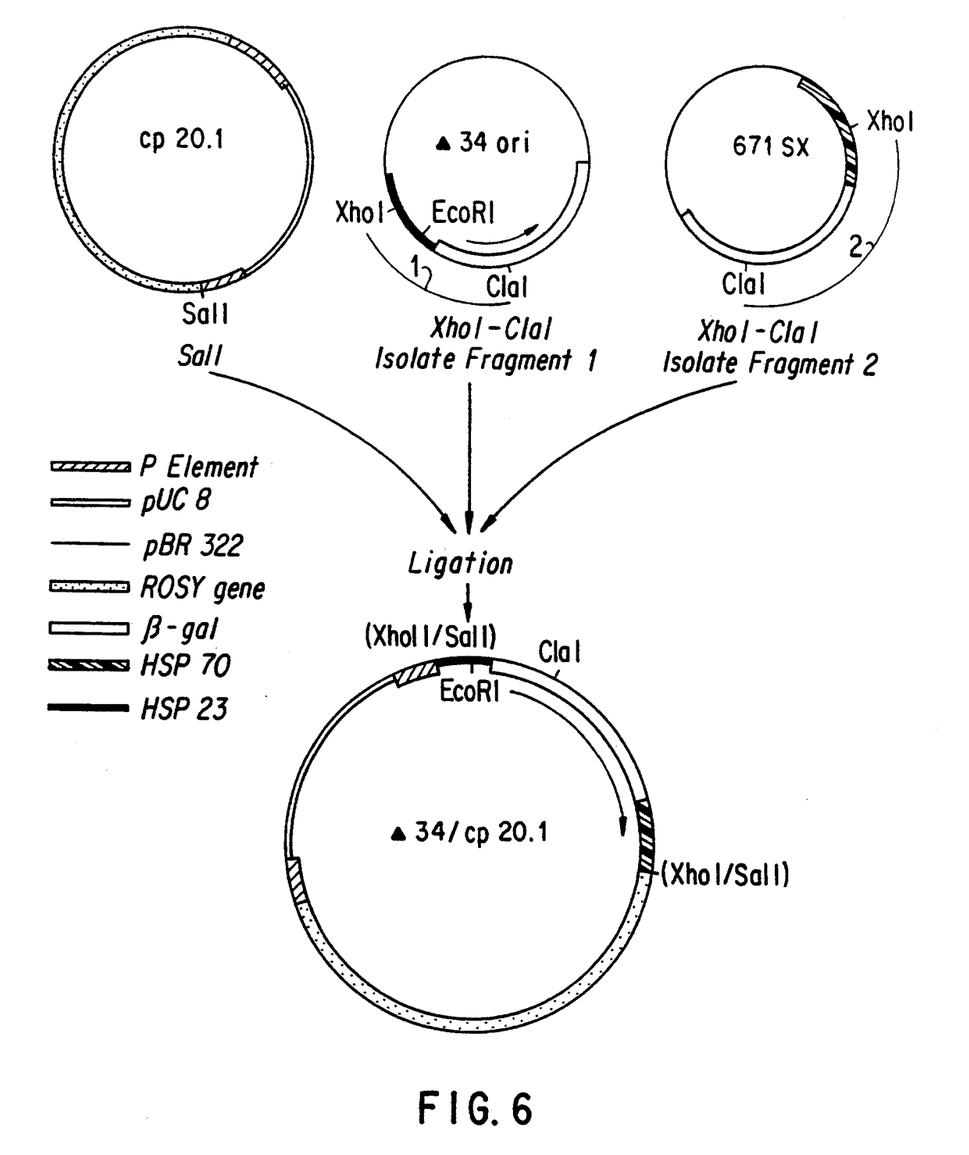
FIG. 6 shows a representative protocol for introducing a 23 kDa heat shock protein- β-galactosidase hybrid gene into a P-element vector.

A number of hybrid 23 kDa heat shock protein-β-galactosidase genes with promoter segments of different lengths (Mestril, R., et al., EMBO J. 5:1667–1673, 1986) were introduced into cp20.1. See Table 1 . FIG. 6 demonstrates the cloning approach using the representative hybrid gene construct D34ori (referred to in Mestril et al., EMBRO J. 5:1667–1673, 1986, as original D379 mutant gene). Twenty μg of cp20.1 DNA were digested with Sal I, phenol- and ether-extracted, ethanol-precipitated, washed, dried, and resuspended in 15 μl of water. DNAs of plasmids D34ori and p671SX (20 μg each) were digested with Cla I and Xho I and subjected to electrophoresis in 1% low-melt neutral agarose gels. Appropriate CNA fragments were extracted by a procedure involving melting of the agarose and phenol extraction of the DNA from the hot agarose solution (Maniatis et al., 1982, supra). The DNAs were ethanol-precipitated and dissolved in 40 μl of water. A ligation reaction of 35 μl containing 2.5 μl of Sal I-cut cp20.1 DNA, 10 μl of the 1.5 kb Cla I/Xho I fragment of D41ori, 10 ||1 of the 3 kb Cla I/Xho I fragment from p671SX, and 2 μl of T4 DNA ligase (New England Biolabs) was incubated overnight at 15° C. After heat inactivation of the ligase, 5 μl of 10 X Sal I buffer, 1 μl of 5mg/ml bovine serum albumin, 9 μl of water, and 6 μl of Sal I enzyme (New England Biolabs) were added. The reaction was incubated for 3 hrs at 37° C. and was subsequently used to transform *E. coli* strain MC1061. Transformed bacteria were plated on LB-plates containing ampicillin (25 μg/ml) and 40 μg/ml X-Gal (5-bromo-4-chloro-3-indolyl-β-D-galactopyranoside).

Blue colonies were selected, and DNA was prepared from them on a small scale. Correct recombinants were identified by restriction digestion and gel electrophoresis.

Figure 7:
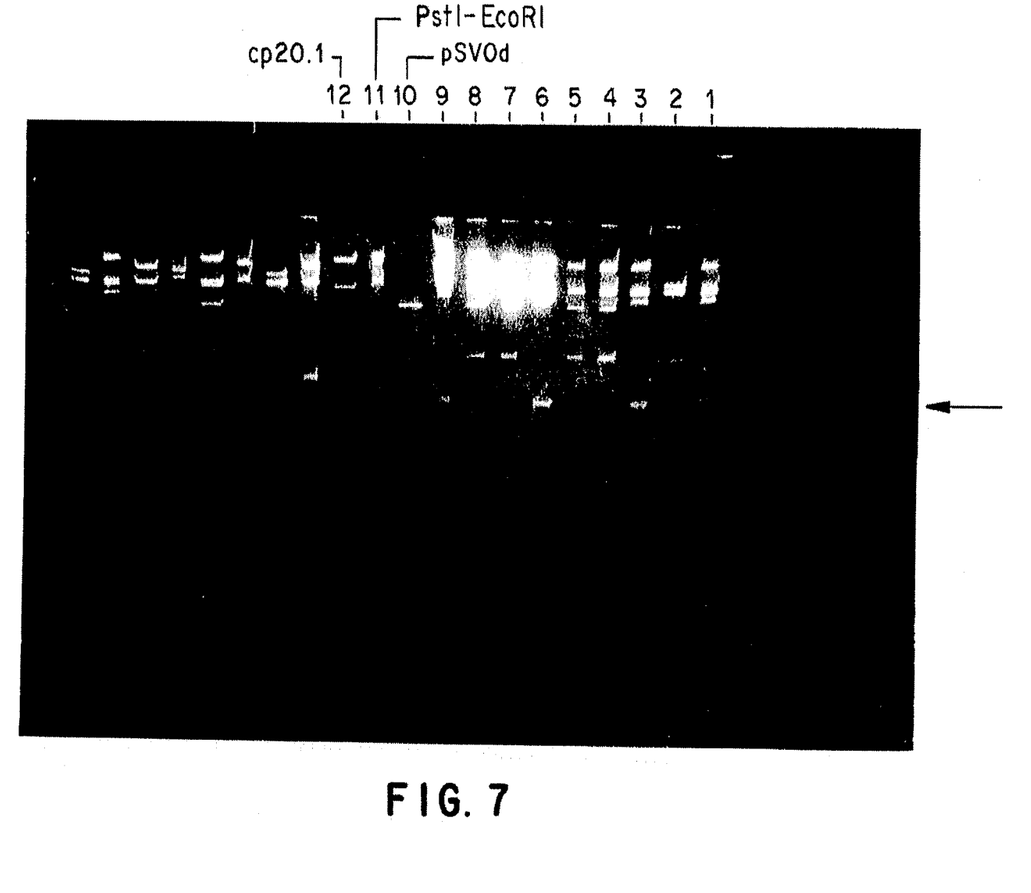
FIG. 7 is a restriction analysis of putative P-element vector derivatives containing the hybrid gene, the lanes depict BamHI digests of putative Δ34-cp20.1 recombinants (lanes 1-9) in an EtBr-stained, 5% acrylamide gel; the arrow indicates bands of interest; lane 10 is a Hinfl digest of plasmid pSVOd (standard), lane 11 is a PstI-EcoRI digest of pSVOd and lane 12 is a BamHI digest of cp20.1.

FIG. 7 shows an example of such an analysis. The distance between the BamH I sites in the cp20.1 polylinker and in the 5' end of the D34ori hybrid gene (the BamH I site is at the junction of the 23 kDa heat shock protein and the β-galactosidase gene sequences) should be about 600 bp if the hybrid gene had been inserted in one particular orientation. A number of recombinants with an extra fragment of this size were identified. Because of frequent recombination events (presumably explained by the large size of the recombinants), recombinants were transformed into recA-negative strain C600 as soon as possible, DNA was prepared on a larger scale from different recombinants by standard procedures, with the final purification of DNA being done by cesium chloride gradient centrifugation.

A list of the cp20.1 derivatives of hybrid genes with 23 kDA heat shock protein gene promoter segments of different lengths is shown in Table 1. The functionality of the genes was tested in cultured *Drosophila melanogaster* S3 cells. Transfected cells were either heat-treated (not shown), exposed for one day at 3 μM ecdysterone, or not treated. Levels of β-galactosidase in extracts were measured by the ELISA procedure described in Mestril et al., *EMBO J.* 5:1667–1673, 1986. Results of such an analysis are included in Table 1. Several of the transfected constructs (those with the longest segments of 23 kDas a protein gene promoter sequence) were active when heat-treated or exposed to ecdysterone and were inactive in untreated cells.

EXAMPLE 3

Preparation of transformed fly strains

The above-described constructs were used to prepare transformed flies using the established procedure of P-element-mediated transformation (Rubin, G. M., and A. C. Spradling, *Science* 218:348–353, 1982) except for some minor changes (Lis, J. T., et al., *Cell* 35:403–410, 1983). Collection of preblastula embryos from ry-negative adult flies were done in half-pint milk bottles modified as follows. The bottoms of these bottles had been cut off and replaced with bridal veil. The cut ends of the bottles were placed on grape agar plates as described by Elgin and Miller (Elgin, S. C. R., and D. W. Miller, Mass rearing of flies and mass production and harvesting of embryos, in The Genetics and Biology of Drosophila, Vol. 2a, Ashburner, M., and T. R. F. Wright, eds., Academic Press, New York, NY, pp. 112–121, 1978), and the flies were allowed to lay their eggs through the veil for periods of 15 to 30 min. Mixtures of plasmids containing a 23 dKa heat shock protein-β-galactosidase hybrid gene at 400 μg/ml and of plasmid Pi15.1 containing a functional transposase gene at 50 μg/ml were injected into the posterior ends of dechorionated embryos attached to coverslips. After injection of coverslips were placed into moist grape agar Petri dishes. Hatched white larvae were transferred to yeast-glucose vials. Transformants were isolated based on the rosy eye color selection procedure. Transformants were homozygosed by standard procedures, and, in the case of recessive, lethal transposition events, stocks were stabilized by balancer chromosomes.

For most transformants the insertion sites of the 23 kDa heat shock-β-galactosidase hybrid genes were mapped by in situ hybridization. Salivary gland squashes were prepared as described in Lis et al. (*Cell* 14:901–919, 1978), and hybridization was essentially as described in Lis et al. (*Cell* 35:403–410, 1983). The hybridization probe was cRNA prepared from the β-galactosidase-plasmid MC931 using ³H-UTP as precursor (42 Ci/mM; Amersham). Results of these in situ experiments are listed in Table 2.

Figure 8:
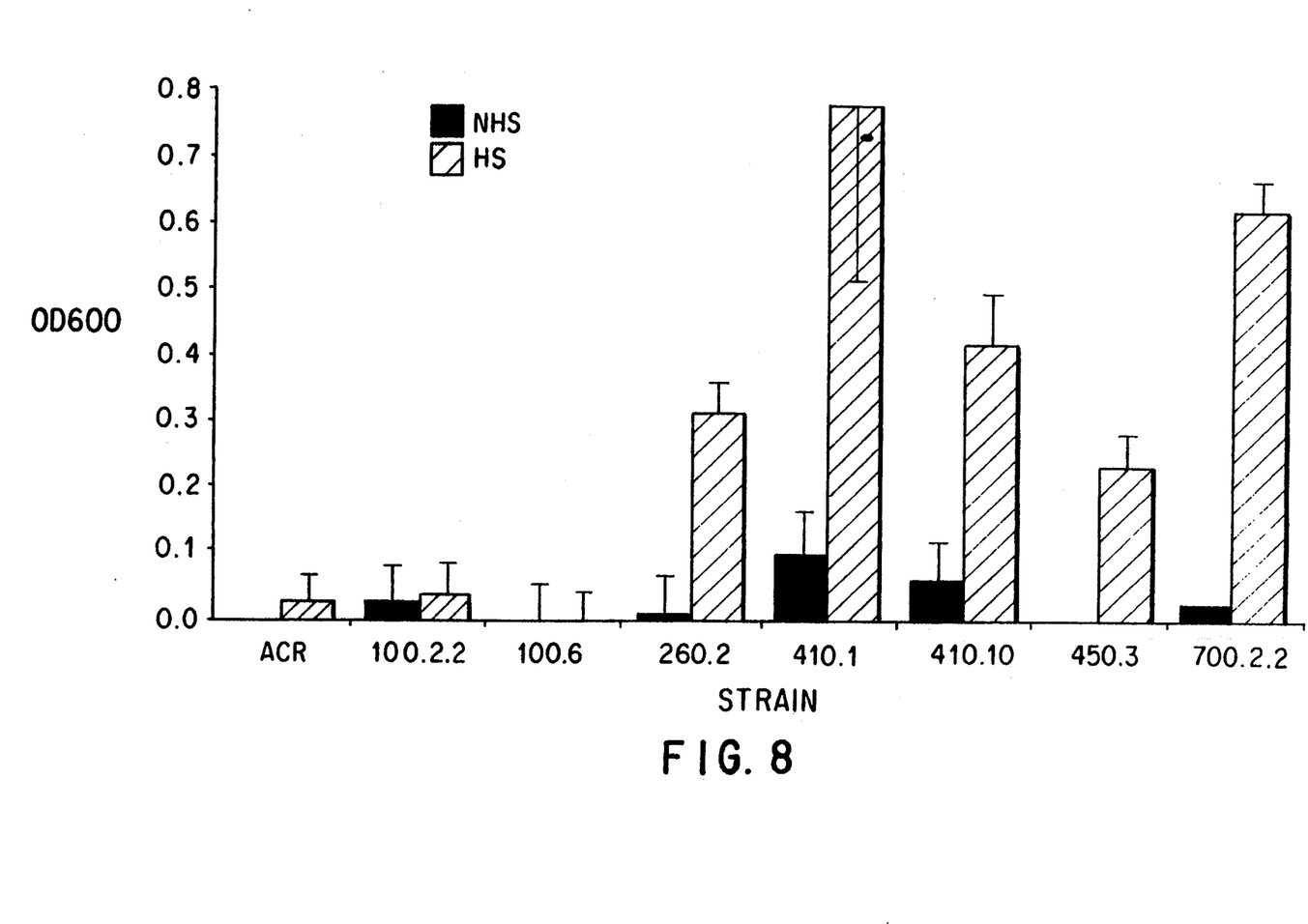
FIG. 8 is a bar graph demonstrating heat-induced expression of various hybrid genes in different transformed fly lines.

X-Gal staining was used to estimate hybrid gene activities in heat treated third instar larvae and adults (Tale 2). The activities of hybrid genes in heat-treated and untreated flies from a number of transformants were also measured by the quantitative β-galactosidase assay described in Lis et al. (*Cell* 35:403–410, 1987). The results from these experiments are in FIG. 8, wherein enzyme activity is plotted on the Y-axis as optical density (OD at 600 nm) for heat shocked (HS) and control NHS) flies.

For the experiments with teratogens described below, only the 700 lines (see Table 2) were used. These lines carry a hybrid gene controlled by a 554 nucleotide-long segment of the 23 kDa heat shock protein gene promoter. Results of these experiments are tabulated in Tables 3 and 4.

EXAMPLE 4

Preparation of embryos, cultures of primary cells, and incubation with teratogens 1. A creamy paste of yeast is placed on a piece of wet filter paper and such coated paper: deposited on 150 mm food plates. Embryos are then collected on these plates for 3 hours (inside a large fly cage). (For additional details, see the appended Materials and Methods section.)

2. The plates with the embryos are incubated further for 3.5 hours (embryos will reach the gastrulation stage).

3. The filter paper containing yeast is discarded. The plates are flooded with water, the embryos are brushed down, passed through a 1 mm (pore size) mesh and then collected on a 90 μm mesh.

4. Embryos are washed extensively with water. Subsequently they are picked up with a spatula and are placed into a solution of 10 ml chlorox/10 ml ethanol (95%). After a brief incubation, the embryos are transferred to a sintered glass funnel attached to a vacuum line and are washed with several volumes of sterile distilled water, No more than 2 minutes should elapse between the first exposure of the embryos to chlorox-ethanol solution and the beginning of the wash steps.

5. The embryos are then washed in 6 ml of culture medium. It is important to note that the embryos are not allowed to dry out during the wash procedure.

6. The wet embryos are transferred with a blunt spatula into a homogenizer containing 7 ml of culture medium. (Alternatively, they can be washed down into the homogenizer with medium.)

7. Three gentle passes are made with the loose fitting pestle.

8. Cell aggregates are broken up by repeated pipetting with a 1 ml pipette, and the cell suspension is passed through a 53 μm mesh.

9. The filtrate is collected in a 15 ml sterile disposable centrifuge tube and spun at 1800 rpm for 4 minutes (at room temperature).

10. The supernatant is decanted, and the cells are washed once more with 4 ml of medium.

11. The cells are finally suspended in 4 ml medium by repeated pipetting with a 1 ml pipette and are counted on a hemocytometer.

12. The cells are plated in 35 mm dishes at a density of $3.2 \times 10^6$ cells per 2 ml of medium.

13. Forty-five minutes later the medium is removed from each dish, and 2 ml of fresh medium containing the chemical to be tested for teratogenicity is added. The culture is then incubated at 22° C. for 20 hrs. In a modification of the procedure, a microsomal fraction is added to this incubation to convert certain compounds into their active form (Bournias-Vardiabasis, N., and J. Flores, *Teratog, Carcinog. and Mutag.* 3:255–262, 1983). The cells are subsequently processed for the β-galactosidase assay (see below).

EXAMPLE 5

Assay of β-galactosidase

1. Cells in 35 mm dishes are washed once with phosphate-buffered saline and are then transferred to 15 ml centrifuge tubes.

2. The cells are collected by centrifugation (clinical centrifuge, 2000 rpm, 5 min) and are taken up in 350 μl of Z buffer (defined below) containing 0.5% of Nonidet NP40. The cells are lysed by repeated pipetting. Lysates are transferred to 1.5 ml Eppendorf tubes.

3. After a 5 minute spin (in the Eppendorf centrifuge) the supernatants are transferred to another set of tubes.

4. To 200 μl of this extract, 275 μl of substrate solution ONPG (4 mg/ml) in Z-buffer is added. The assays are run with straight as well as with diluted extract samples.

5. The reactions are incubated at 37° C. for 30 min.

6. The reactions are stopped by the addition of 170 μl of 1 M sodium carbonate.

7. Optical density readings of the clarified supernatant are taken at 420 and 550 nm.

8. Activity of β-galactosidase is calculated using the equation $A_{420} - 1.1 \times A_{550}$. Specific enzyme activities can be calculated following determination of protein concentrations in extracts.

Materials for the assay:

1. 15 ml centrifuge tubes, 1.5 ml Eppendorf centrifuge tubes (Sarstedt).

2. Z-Buffer; $Na_2HPO_4$ (60 mM), $NaH_2PO_4$ (40 mM), KCl (10 nM), $MgSO_4$ (1 mM), and 2-mercaptoethanol (50 mM). The buffer should have a pH of 7.

3. O-nitrophenyl galactopyranoside (ONPG) from Sigma.

4. 1 M $Na_2CO_3$, from Sigma.

5. Equipment: clinical centrifuge, Eppendorf centrifuge, water bath incubator, spectrophotometer (visible), pipette aid.

Protein assay:

Total protein was estimated from 10 μl aliquots of cell extracts using the Biuret kit from BioRad.

EXAMPLE 6

Alternative assay for β-galactosidase

Following the manipulations described in Example 5, extracts are prepared from the cultured cells following exposure to substances with teratogenic potential. Concentrations of marker gene products in these extracts are then determined by immunological methods such as ELISA using specific antibodies for the marker gene products. A suitable ELISA procedure capable of detecting the activity of 23 kDa Drosophila heat shock protein-β-galactosidase hybrid genes in transfected Drosophila cells is described in Mestril et al., *EMBO J.* 5:1667–1673, 1986.

Materials and Methods

1. Plexiglas (2 cu. ft.) or glass aquariums (10"×20"×12") to be used as fly cages.

2. Drosophila food: corn meal, sugar, yeast, or grape juice, purchased from local supermarket. Agar; from Gibco.

3. Schneider's Drosophila medium for cell culture; from Applied Scientific, CA.

4. Petri dishes for food plates or grape juice plates (egg collection); from Falcon.

5. Brush, camel's hair, 0.5 to 0.75 inch in length.

6. Meshes with openings of 53 μm, 90 μm, and 1 mm; Tetco. CA.

7. Glassware: funnel (Hirsch type with coarse fitted disc), thick-walled filter flask, beakers (50 ml), sterile pipettes, standard glass funnel (Corning).

8. Homogenizer, Tenbroeck type, 150 mm Clearance; Corning.

9. Spatula, rubber corks and tubings, sterile cell scrapers.

10. Tissue culture dishes, 35 mm; from Corning.

11. 15 ml conical, disposable centrifuge tubes; Sarstedt.

12. Fetal bovine serum; Gibco. Not every batch can be used for the experiments: superior batches need to be identified by testing for in vitro differentiation of embryonic cells.

13. Insulin (Sigma Cat. #16634); L-glutamic acid (Sigma Cat. #G5763); mold inhibitor from Carolina Biologicals.

14. Chlorox (sodium hypochlorite 5.25%).

15. Ethyl alcohol 95%.

16. Filter paper: Whatman No. 1.

17. Equipment: clinical centrifuge, microscope, hemocytometer, fly incubator at 25° C.; the light and dark cycle can be adjusted by using a light attached to a timer.

18. Embryo collection: the 1 mm- and 90 μm-meshes are supported by a plexiglas cylindrical frame with a diameter of about 10 cm, so that the wide mesh is positioned over the narrow one.

19. For collecting single cells after Dounce homogenization, the 53 μm mesh is supported by a metallic, split O-ring that is positioned in an appropriate glass funnel. A centrifuge tube is positioned below the funnel to collect the single cells.

20. Food plates and boxes. Sugar (80 g), corn mean (80 g), yeast (20 g) and agar (7g) are cooked in 1 l of water for 35 min. Mold inhibitor (1 g) dissolved in as little ethanol as possible is added, and the food is cooked for an additional 5 min. Stirring during cooking is advisable. Pour food into Petri dishes to a height of about ½ inch in 10"×5"×4" plastic boxes (Rubbermaid). Openings of 2"×6" are cut out from the lids and are covered with a 90-μm mesh that is held in place by adhesive tape.

21. Maintaining population cages. Plexiglas or glass aquariums have been transformed into standard fly cages. About 30 gm of male and female flies are introduced in a cage. The cages are placed in a moist environment at a temperature of 25° C. A 12-hr light-and-dark-cycle is maintained. Embryos for the assay are collected in the early hours of the light cycle during the first three hours when the egg laying is at its peak. For maintenance of the fly cultures embryos are collected overnight are then transferred to the plastic food boxes spread with fresh yeast paste. After about two weeks the eclosed flies are transferred again to a large cage for use in teratogen assays. The peak egg laying period is two weeks posteclosion. Thus, a convenient schedule can be worked out to ensure a continuous supply of flies for egg collection. Cleaning of old cages is facilitated by cooling them to 4° C. (to collect fly bodies at the bottom of the cages).

22. Grape juice plates for egg collection: grape juice (800 ml from the local supermarket), water (800 ml). and agar (32 g) are heated to boiling. 16 ml each of 95% ethanol and of acetic acid are added, and the medium is then poured into 150 mm Petri dishes.

23. Drosophila culture medium: powdered Schneider's medium (11.55 g) and L-glutamic acid (0.9 g) are dissolved in 500 ml of sterile distilled water, and the pH is adjusted to 6.6 with 1 M KOH. 1 ml of tissue culture grade penicillin-streptomycin mixture is added, and the medium is sterile-filtered. Shortly before use, insulin (10 μl of a 2 mg/ml solution of 0.05 N HCl; Sigma) and fetal bovine serum (18 ml) are added to 100 ml of medium.

While the preferred embodiments of the invention have been illustrated and described, it is to be understood that within the scope of the appended claims various changes and substitutions of equivalents can be made. Hence, the invention can be practiced in ways other than those specifically described herein.

TABLE 1

Activities of 5' deletion mutants in vector cp20.1 in transfected D. melanogaster S3 cells

| Length of 5' nontranscribed segment (bp) | E. coli-specific + ecdysterone | B-galactosidase − ecdysterone |
|---|---|---|
| 554 | 1.0 | |
| 379 | 2.0 | 0.1 |
| 363 | 1.1 | |
| 333 | 1.0 | 0.0 |
| 295 | 0.6 | |
| 275 | 0.3 | |
| 197 | 0.1 | |
| 147 | 0.1 | |
| 63 | 0.1 | 0.0 |

Levels of B-galactosidase were measured in cell extracts using the ELISA protocol described in Mestril et al., 1986 (Mestril,R., Schiller,P., Amin,J., Klapper,H., Ananthan,J. and Voellmy,R. (1986) EMBO J. 5:1667-1673).

TABLE 2

Expression of B-galactosidase in heat-treated larvae and adults of hybrid-gene-transformed Drosophila melanogaster strains

| Sub-strain | Names of mutant genes | Third Instar Larvae | Adult | Locus | Balancer |
|---|---|---|---|---|---|
| 60.1.1 | d140 | − | − | 30 D | + |
| 90.3 | d139 | − | − | 102 D | + |
| 90.4 | d139 | − | − | 54 | + |
| 100.1 | d63 | − | − | 33 A | + |
| 100.3.1 | d63 | − | − | 85 D | Ubx |
| 100.4 | d63 | − | − | 3 B | + |
| 100.5 | d63 | − | − | | + |
| 260.2.2 | d274 | + | ++ | 79 E/F | + |
| 280.3 | d295 | + | + | 45 B/C | + |
| 370.1 | d333 | + | ++ | 68 F | + |
| 370.2 | d333 | + | + | 19 D | + |
| 370.3.1 | d333 | ++ | ++ | 79 E | + |
| 410.1 | d363 | + | +++ | 79 F | + |
| 410.4 | d363 | ++ | ++ | 11 C | + |
| 410 10 | d363 | + | + | 5 D | + |
| 450.1 | d379 | + | + | Chromc. | |
| 700.1.2 | d554 | | +++ | 86 E | Ubx |
| 700.2 | d554 | | +++ | | |

Expression of B-galactosidase was estimated by in situ staining of larval and adult tissues in an X-Gal solution.

TABLE 3

EVALUATION OF THE TERATOGENIC POTENTIAL OF REPRESENTATIVE SUBSTANCES USING THE DROSOPHILA HEAT SHOCK HYBRID GENE EXPRESSION ASSAY. EXPERIMENT I

| TREATMENT | CONC. mM | CLASS | FOLD INDUCTION OF B-GAL ACTIVITY |
|---|---|---|---|
| COUMARIN | 1.0 | T | 5 |
| DIPHENYL-HYDANTOIN | 0.1 | T | 2 |
| B-ECDYSTERONE | 0.01 | T | 2 |
| RETINOIC ACID (ALL TRANS) | 0.05 | T | 5 |
| ARSENATE | 0.2 | T | 8 |
| Hg Cl$_2$ | 0.005 | T | 3 |
| Cd Cl$_2$ | 0.25 | T | 7 |
| DIETHYL STILBOSTEROL | 0.01 | T | 7 |
| ACETYL SALICYCLIC ACID | 1.0 | NT (weak T) | 1.5 |
| 5-DEOXY-2' AZACYTIDINE | 0.01 | T | 4 |
| PROGESTERONE | 0.01 | NT | 1.0 |
| ETHYL ALCOHOL | 160 | NT | 1.2 |
| DIMETHYL SULFOXIDE | 1.0 | NT | 1.0 |
| HEAT SHOCK | 30 min | T | 7 |

Embryonic cells from the transformed fly strain 700.2 were prepared and were exposed to the above substances for 20 hrs as described in the text. The data shown were derived from colormetric B-galactosidase assays that had been performed on extracts from cells treated or not-treated with substances. Enzyme activities in treated cells are expressed relative to those in non-treated cells. Substances that have been shown to be teratogenic in animal experiments are labeled "T" (for teratogen), and those that are non-teratogenic "NT".

TABLE 4

EVALUATION OF THE TERATOGENIC POTENTIAL OF SUBSTANCES USING THE DROSOPHILA HEAT SHOCK HYBRID GENE EXPRESSION ASSAY. EXPERIMENT II

| Compound/Treatment | Concentration mM | Fold Induction of B-Gal Activity |
|---|---|---|
| Zinc | 1 | No induction |
| Lead | 2.5 | 15.78 |
| Caffeine | 1 | 1.02 |
| Valium | 1 | 6.5 |
| Thalidomide | 1 | 2.73 |

For explanation, see Table 3.

The embodiments of the invention in which an exclusive property or privilege is claimed are defined as follows:

1. A method of screening a test substance for potential teratogenicity, comprising the steps:
   providing primary embryonic cells from a Drosophila transformed via a P element with a hybrid gene comprising a coding sequence for a detectable expression product under the control of the promoter and leader sequence of the 23 kDa Drosophila heat shock protein gene,
   exposing said primary embryonic cells in vitro to the test substance, and
   assaying in vitro for the detectable expression product in the cells, the presence of the expression product in the cells providing an indication of the potential teratogenicity of the test substance.

2. The method of claim 1, wherein the detectable expression product is assayed by enzymatic means.

3. The method of claim 1, wherein the detectable expression product is assayed by immunologic means.

* * * * *